United States Patent [19]

Chen et al.

[11] Patent Number: 4,948,787

[45] Date of Patent: Aug. 14, 1990

[54] INHIBITION OF MERCAPTAN ODOR IN ORGANOTHIOPHOSPHATE BIOCIDES

[75] Inventors: Chia-Chung Chen, Hercules; Richard H. Rider, El Cerrito; Ray J. Lo, Alameda, all of Calif.

[73] Assignee: Imperial Chemical Industries PLC, London, England

[21] Appl. No.: 293,244

[22] Filed: Jan. 4, 1989

[51] Int. Cl.$^5$ .................... A01N 57/00; A01N 57/10; A01N 57/18; A01N 23/00

[52] U.S. Cl. ........................ 514/141; 514/80; 514/144; 514/148; 514/769; 558/214

[58] Field of Search .................. 424/601, 667, 644; 514/75, 80, 141, 144, 148, 769

[56] References Cited

U.S. PATENT DOCUMENTS

| | | | |
|---|---|---|---|
| 2,759,010 | 8/1956 | Lorenz et al. | 260/461 |
| 2,767,194 | 10/1956 | Fancher | 260/326 |
| 2,988,474 | 6/1961 | Szabo et al. | 167/30 |
| 3,642,960 | 2/1972 | Pitt et al. | 260/985 |
| 4,370,301 | 1/1983 | Doi et al. | 422/3 |
| 4,752,604 | 6/1988 | Chavdarian et al. | 514/141 |

*Primary Examiner*—Douglas W. Robinson
*Assistant Examiner*—Zohreh A. Fay
*Attorney, Agent, or Firm*—Denis A. Polyn

[57] ABSTRACT

Mercaptan odors in a thiophosphate compound or formulation are suppressed by treatment of the compound during preparation of the formulation with treatment agents selected from iodine, and alkali and alkaline earth metal hydroxides, hypochlorites and iodates. Depending on the particular agent and method of treatment used, the agent and any reaction products resulting from the treatment may be either removed from the thiophosphate or retained with it in the final formulation. Formulations of particular interest are granular formulations for field application.

35 Claims, No Drawings

INHIBITION OF MERCAPTAN ODOR IN ORGANOTHIOPHOSPHATE BIOCIDES

This invention relates to thiophosphate biocides, and in particular to agricultural formulations of biocidal thiophosphate which have a tendency to emit mercaptan vapors.

BACKGROUND OF THE INVENTION

Organothiophosphate insecticides are well known and widely used for crop protection. Included among these are Counter (terbufos), Thimet (phorate), Mocap (ethoprop), Torak (dialifor), Trithion (carbophenothion), Nialate (ethion), Navadel (dioxathion), Dyfonate (fonofos), and Imidan (phosmet).

An unfortunate aspect of many of these compounds is a mercaptan odor. The presence of mercaptans in compositions or formulations of these compounds is due to a number of factors. In some cases, the mercaptans serve as starting materials for the synthesis of these compounds, and their presence in the final product is the result of trace amounts of unreacted starting material. These compounds also tend to degrade or decompose to produce mercaptans, particularly when subjected to heating or conditions promoting acid hydrolysis. Still further, thiophosphite analogs of the compounds are present in some cases as by-products of the synthesis, and these thiophosphite species have a high tendency to decompose to mercaptans. Regardless of the mechanism by which the mercaptan odor is produced, it is undesirable from an environmental point of view as well as for handling and field application purposes.

SUMMARY OF THE INVENTION

It has now been discovered that mercaptan odor development in an organothiophosphate compound or formulation is suppressible by treatment of the compound during preparation of the formulation in which it will be applied. In particular, it has been discovered that certain treatment agents may be applied to the compound during its formulation procedure to remove any mercaptan present and any other species having a high tendency to release mercaptan. These agents, which may be applied individually or in combination, include iodine, and alkali and alkaline earth metal hydroxides, hypochlorites and iodates. The treatment method will vary depending on the agent used, in accordance with the treatment mechanism. Similarly, the type of formulation to which the treatment may be applied may vary as well. The result in any case is a formulation which is initially free of mercaptan odor and in which the timewise development of mercaptan odor is inhibited if not eliminated entirely.

DETAILED DESCRIPTION OF THE INVENTION AND PREFERRED EMBODIMENTS

In one aspect of the present invention, the thiophosphate composition is treated with iodine to accelerate any latent mercaptan production in the composition. This treatment is particularly effective in compositions where mercaptan production is primarily the result of thiophosphite impurities included with the thiophosphate.

The iodine is added in the zero-valent form. Examples include molecular iodine ($I_2$) and triiodide. In preferred embodiments, the iodine is applied as molecular iodine in a non-polar solvent. Examples of such are paraffins, toluene, xylenes and aromatic naphthas, notably heavy aromatic naphthas. The method of treatment is not critical and may vary widely. For example, a two-phase system may be used, whereby the thiophosphate is present as a solution in a non-polar organic solvent and the triiodide is present in polar aqueous solution. The two phases are brought into contact in a manner sufficient to achieve maximal interfacial contact, then phase separated.

Any generated mercaptan which remains in the non-polar organic phase may then be removed by conventional means, such as distillation. Alternatively, excess iodine may be used to convert the undistilled mercaptan to the corresponding disulfide. The disulfide will be odorless and may thus be retained with the thiophosphate, rather than removed. For this alternative, the iodine is preferably used as a solution in a polar solvent.

The polar solvent may be any conventional, inert, and otherwise agriculturally acceptable material. Examples are water and polyols such as ethylene glycol, triethylene glycol, propylene glycol, dipropylene glycol, dibutylene glycol, hexylene glycol and triethanolamine. The polyols are further useful as stabilizing agents for granular products of the thiophosphate on clay to inhibit the decomposition of the thiophosphate to generate mercaptans.

In particularly preferred embodiments of this aspect of the invention, the thiophosphate compound (including impurities such as unreacted starting material, synthesis by-products, and degradation products) is combined with small amounts of iodine, polar stabilizer, and non-polar solvent, and agitated to first release mercaptan and to subsequently convert mercaptan to disulfide, then combined with an inert diluent or carrier as typically included in an agricultural formulation.

The relative amounts of these components are not critical, and may vary widely. The optimal amount of iodine used will of course be selected in accordance with the amount of mercaptan or thiophosphite by-product included with the thiophosphate, and whether or not the iodine is also intended to oxidize the resulting mercaptan to the disulfide form. Likewise, the optimal amount of solvent and stabilizer will depend on economic and activity considerations as well as the type of formulation ultimately prepared. In most applications, an amount of iodine which comprises from about 0.1 to about 10 parts by weight per 100 parts by weight of the active ingredient (i.e., the thiophosphate itself), preferably from about 0.3 to about 3 parts per 100 parts, will provide the best results. Similarly, formulations where the non-polar solvent and the polar stabilizer each comprise from about 5 to about 100 parts by weight per 100 parts by weight of the active ingredient, preferably from about 20 to about 60 parts per 100 parts, will generally provide the best results. A typical formulation, for example, may be a granular formulation in which the iodine comprises about 0.1–0.3%, the active ingredient about 15.23%, the non-polar solvent about 6%, and the polar stabilizer about 6%, the remainder being the dry granule.

In a second aspect of the invention, an alkali metal or alkaline earth metal hydroxide is the treatment agent. Preferred among these are sodium and potassium hydroxides, particularly sodium hydroxide. Treatment according to this aspect of the invention is done by conversion of the mercaptan to the corresponding alkali or alkaline earth metal mercaptide, and extraction of the mercaptide from the thiophosphate-containing phase. The treatment is thus preferably performed in two at least substantially immiscible liquid phases, one containing the thiophosphate and the other the hydroxide.

The phase containing the thiophosphate compound is preferably a solution of the compound in a non-polar solvent. Examples of such solvents are paraffins, xylenes and aromatic naphthas, notably heavy aromatic naphthas. The phase containing the hydroxide is preferably a solution in a polar solvent, water being preferred. Particularly preferred is an aqueous sodium hydroxide solution at a concentration of from about 2% to about 15% by weight. The phases are sufficiently contacted to achieve equilibrium, then separated by conventional means.

A stabilizing agent is preferably included in the final composition here as well. Those stabilizing agents listed above are preferred.

In a third aspect of the invention, the treatment agent is a hypochlorite or an iodate of an alkali or alkaline earth metal. Preferred among these are alkali metal hypochlorites and iodates. Preferred alkali metals are sodium and potassium, with sodium particularly preferred.

Treatment according to this third aspect of the invention results in oxidation of the mercaptan to one or more of several forms, including the disulfide, the various analogs of the disulfide with one or both of the sulfur atoms in a more highly oxidized state up to the disulfone, and the sulfur acids up to the sulfonic acid. None of these oxidation products are malodorous. As a result, they may either be removed from the thiophosphate or retained with it in the final formulation.

Treatment of the thiophosphate in accordance with this third aspect of the invention may be done in the manner described above for the alkali and alkaline earth metal hydroxides. As in that aspect, system parameters such as solvents and concentrations may vary widely. The optimal parameters for any given application will generally depend on the particular system, i.e., the specific thiophosphate used, the treatment agent, and the nature of the formulation ultimately produced. As one example, when sodium hypochlorite is used, best results will generally be obtained using an aqueous solution at a concentration of about 0.1% to about 2.0% by weight. As another example, when potassium iodate is used, best results will generally be obtained with an aqueous solution at a concentration of about 1.0% to about 5.0% by weight.

The treated thiophosphate is incorporated into a formulation suitable for application for biocidal purposes. Any of the wide range of formulations developed for thiophosphates may be employed, using the formulating procedures and ingredients conventionally used and disclosed in the literature for this type of biocide. A major part of any such formulation is an inert diluent or carrier, which may take on any of a variety of forms, depending on the formulation. The inert diluent or carrier may thus be liquid or solid, for example, solvents, liquid carriers forming emulsions of the active ingredient, dusts, wettable powders, porous granules, and microcapsules. The formulation may be a controlled-release formulation, and the active ingredient may be combined with other active ingredients for synergistic effects or for combining the biocidal activity of the thiophosphate with different types of biological activity, such as other types of biocidal activity, broadening of the pest control spectrum, and the inclusion of crop fertilizers or growth regulators.

The treated thiophosphates of the present invention are of particular interest for use in granular formulations. Any of the wide range of granular carriers known among those skilled in the art may be used. Examples include fuller's earth, attapulgite clay, bentonite clay, montmorillonite clay, kaolin, diatomaceous silicas, vermiculite, and perlite. The active ingredient is generally applied in liquid form, and is sprayed, absorbed or applied as a coating to the granular carrier to achieve levels ranging from about 5% to about 25% by weight. Other ingredients are generally included to enhance the application or absorption process as well as to enhance retention of the active ingredient or its dispersion throughout the region where biocidal control is desired, depending on the circumstances.

The thiophosphates to which the present invention is applicable include the wide range of biocidally active thiophosphate compounds which are susceptible to the emission of mercaptan odors, either as a result of their synthesis, the presence of synthesis by-products, or as a result of the degradation of either the thiophosphate or any of the by-products present as impurities. These thiophosphates will generally contain at least one sulfur atom bonded directly to the phosphorus atom through a single bond. The term "thiophosphates" is used herein in a broad sense to include all such compounds. Subclasses of these compounds include thionophosphates, thiolophosphates, thionophosphonates, and thiolophosphonates, and mixtures thereof.

In particular, the thiophosphate will generally be one having the formula

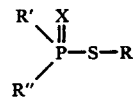

in which X is O or S, and R, R' and R" are independently any of a wide variety of organic radicals, including aliphatic, aromatic, N-containing, S-containing, O-containing, and other groups, including substitutions such as halogen, trifluoromethyl, cyano, etc. Each of the groups R' and R" may also contain a sulfur atom directly adjacent to the phosphorus atom. Examples of compounds within the above formula are found in Lorenz, et al., U.S. Pat. No. 2,759,010 (Aug. 14, 1956); Chavdavarian, et al., U.S. Pat. No. 4,752,604 (June 21, 1988); Fancher, U.S. Pat. No. 2,767,194 (Oct. 16, 1956); Pitt, et al., U.S. Pat. No. 3,642,960 (Feb. 15, 1972); Szabo, et al., U.S. Pat. No. 2,988,474 (June 13, 1961); Diveley, et al., U.S. Pat. No. 2,725,328 (Nov. 29, 1955); Jamison, U.S. Pat. No. 3,355,353 (Nov. 28, 1967); Fancher, U.S. Pat. No. 2,793,224 (May 21, 1957); and Willard, et al., U.S. Pat. No. 2,873,228 (Feb. 10, 1959). These patents are incorporated herein by reference.

The present invention is of particular interest in connection with thiophosphates having the formula

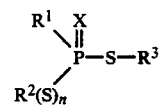

in which $R^1$ is methyl or ethyl, $R^2$ is tertiary alkyl having 4 to 6 carbon atoms, $R^3$ is tertiary alkyl having 4 to 6 carbon atoms, X is sulfur or oxygen, and n is zero or one. Of particular interest within this formula are S,S-(di-t-butyl) methylphosphotrithioate, in which $R^1$ is methyl, $R^2$ is tertiary butyl, $R^3$ is tertiary butyl, X is sulfur, and n is one; and S,S-(di-t-butyl) ethylphosphotrithioate, in which $R^1$ is ethyl, $R^2$ is tertiary butyl, $R^3$ is tertiary butyl, X is sulfur, and n is one. Other thiophosphates of interest are Counter (terbufos), Thimet (phorate), Mocap (ethoprop), Torak (dialifor), Trithion (carbophenothion), Nialate (ethion), Navadel (dioxathion), Dyfonate (fonofos), and Imidan (phosmet).

The following examples are offered for purposes of illustration, and are intended neither to limit nor define the invention in any manner.

EXAMPLE 1

This example illustrates the preparation of a granular formulation of the insecticide S,S-(di-t-butyl) methylphosphotrithioate, including treatment with molecular iodine.

A stock solution of the phosphotrithioate technical (approximately 94% in purity) was prepared by dissolving 430 g of the technical material in 188 g of SURE SOL 190, a heavy aromatic solvent naphtha supplied by Koch Chemical Company. A portion of this solution (46 g) was combined with 0.4 g of molecular iodine solid and was mixed thoroughly. The resulting solution was then treated with 12 g of dipropylene glycol and applied to 142 g of AGSORB 24/48 LVM-MS, a granular montmorillonite clay granule supplied by Oil-Dri Corporation. These amounts were calculated to produce granules containing approximately 15% by weight of the active ingredient.

A control granular sample was also prepared, following the procedure described in the preceding paragraph without the inclusion of the molecular iodine.

Various tests for mercaptan, all using commercially available materials and conventional procedures well known among those skilled in the art, were conducted to determine mercaptan levels in the granules and in the vapor space above the granules. These tests included a copper sulfate test and a Draeger tube test to determine the mercaptan level in the vapor space. Conventional gas chromatography (GC) was also applied to determine the mercaptan level both in the granule and in the vapor space. The results of the mercaptan detection were as follows:

| | Copper Sulfate | Draeger test | GC Analysis |
|---|---|---|---|
| Control sample | positive | positive | positive |
| Iodine-treated sample | negative | negative | negative |

EXAMPLE 2

This example illustrates a similar treatment using triiodide.

The same phosphotrithioate solution used in Example 1 (27 g) was combined and mixed with 27 g of an aqueous triiodide solution prepared by dissolving 1 g of sodium iodide in 1 g of water and combining this with 0.34 g of molecular iodine in 25 g of water. The solutions were then phase separated, and the organic phase was washed with 27 g of 5% aqueous sodium carbonate solution. After a final phase separation, the organic phase was treated with dipropylene glycol and then used to impregnate clay granules in the same manner as described in Example 1, using the same materials and proportions.

After 3 days, the granules tested negative for mercaptan in both the $CuSO_4$ and Draeger tube tests. After 4 days at 125° F., the granules still gave negative results in both tests.

EXAMPLE 3

This example illustrates a similar treatment using aqueous iodine solution.

The same phosphotrithioate solution used in Example 1 (30 g) was combined with 30 g of an aqueous solution of iodine, prepared by dissolving 0.5 g of $I_2$ in 5 g of acetone, then adding 50 g of water. The two phases were mixed thoroughly, then separated. The resulting nonaqueous phase was then treated with 8 g of dipropylene glycol and applied to 90 g of clay as described in Example 1. Negative mercaptan test results were obtained using the copper sulfate and Draeger tube methods.

EXAMPLE 4

This example illustrates a test involving the liquid insecticide S,S-(di-t-butyl) ethylohosphotrithioate, without treatment for mercaptan suppression, for purposes of comparison.

The phosphotrithioate (16 g) was combined with 1 g of SURE SOL 190 and mixed thoroughly. The resulting solution gave positive test results for mercaptan in copper sulfate, Draeger tube and GC tests.

EXAMPLE 5

This example illustrates tests involving the same insecticide as Example 4, except that treatment with iodine was included.

A bottle was charged with 16 g of the technical phosphotrithioate, 1 of SURE SOL 190, and 0.1 g of solid iodine. The resulting solution was mixed for three days, after which copper sulfate, Draeger tube and GC tests for mercaptan indicated positive.

In a separate test, a bottle was charged in the identical manner except that 8 g of dipropylene glycol was added. After three days, the detection tests for mercaptan from this solution were negative.

EXAMPLE 6

This example illustrates treatment with sodium hydroxide, using the same insecticide as Example 1.

A stock solution of the technical phosphotrithioate was prepared in the same manner as Example 1. A 30-g portion of the stock solution was combined with 30 g of a 10% aqueous sodium hydroxide solution. After thorough mixing, the two solutions were phase separated. A granular formulation containing 15% active ingredient was then prepared in the same manner as Example 1. In copper sulfate and Draeger tube tests, the sample showed a slightly positive indication of mercaptan. GC analysis indicated that the mercaptan level in the vapor space of this treated granule was approximately 10% of that of the untreated control sample.

EXAMPLE 7

Example 6 was repeated, except that 2% aqueous sodium hypochlorite was used in place of 10% aqueous sodium hydroxide. The resulting granule tested slightly positive in the mercaptan detection tests.

EXAMPLE 8

This example illustrates an iodine treatment of Mocap 15G, a commercial product of Rhone Poulenc Inc. This product is a granular formulation of O-ethyl S,S-dipropyl phosphorodithioate with an active ingredient level of 15 weight percent.

A solution (20 g) of 1% iodine in n-hexane was added to 50 g of Mocap 15G granules either by spraying or dripping. The granules were then mixed in a rotating container for three hours. A copper sulfate test was then conducted, and the results indicated substantially reduced mercaptan levels when compared to an untreated control sample.

The experiment was repeated, using methylene chloride as the solvent in place of n-hexane. The same mercaptan reduction was observed as in the first experiment.

EXAMPLE 9

This example illustrates an iodine treatment of Imidan technical material, N-(mercaptomethyl)phthalimide S-(O,O-dimethylphosphorodithioate).

A solution of 20 g of Imidan technical in 40 g of toluene was treated with 0.2 g of solid iodine. The solution was mixed thoroughly, then combined with an aqueous solution (60 g) of 5% sodium carbonate in water. The two phases were mixed, then phase separated. Stirring of the organic phase was continued at ambient temperature to volatilize the solvent. Once evaporation was complete, the recovered Imidan technical solid had very low mercaptan odor.

The foregoing descriptions are offered primarily for purposes of illustration. It will be readily apparent to those skilled in the art that additional structures as well as modifications and substitutions in the materials, system parameters, and procedures herein described may be made without departing from the spirit and scope of the invention.

What is claimed is:

1. A method for preparing a formulation of a biocidal thiophosphate composition substantially free of mercaptan from contaminants, said method comprising:
   (a) contacting a first solution comprising an alkali or alkaline earth metal hydroxide in a first solvent with a second solution comprising said thiophosphate composition in a second solvent substantially immiscible with said first solvent, to convert substantially all mercaptan in said second solution to the corresponding alkali metal mercaptide in said first solution;
   (b) recovering said second solution from said first solution; and
   (c) combining said second solution with an inert diluent or carrier.

2. A method in accordance with claim 1 in which said first solution comprises a member selected from the group consisting of sodium and potassium hydroxides in said first solvent.

3. A method in accordance with claim 1 in which said first solution comprises sodium hydroxide in said first solvent.

4. A method in accordance with claim 1 in which said second solvent is a member selected from the group consisting of paraffins, xylenes and aromatic naphtha.

5. A method in accordance with claim 1 in which said first solvent is water and said second solvent is a member selected from the group consisting of paraffins, xylenes and aromatic naphtha.

6. A method in accordance with claim 1 in which said first solution is an aqueous sodium hydroxide solution containing from about 2% to about 15% sodium hydroxide by weight.

7. A method in accordance with claim 1 further comprising combining said second solution with a member selected from the group consisting of ethylene glycol, triethylene glycol, propylene glycol, dipropylene glycol, dibutylene glycol, hexylene glycol, and triethanolamine.

8. A method in accordance with claim 1 in which step (c) comprises impregnating porous granules with said second solution.

9. A method in accordance with claim 1 in which said thiophosphate composition comprises a thiophosphate compound having the formula

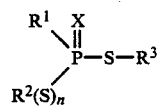

in which $R^1$ is methyl or ethyl, $R^2$ is tertiary aklyl having 4 to 6 carbon atoms, $R^3$ is tertiary alkyl having 4 to 6 carbon atoms, X is sulfur or oxygen, and n is zero or one.

10. A method in accordance with claim 1 in which said thiophosphate is S,S-(di-t-butyl) methylphosphorotrithioate.

11. A method in accordance with claim 1 in which said thiophosphate is S,S-(di-t-butyl) ethylphosphorotrithioate.

12. A method in accordance with claim 1 in which said thiophosphate is N-(mercaptomethyl)-phthalimide S-(O,O-dimethylphosphorodithioate).

13. A method in accordance with claim 1 in which said thiophosphate is O-ethyl S,S-dipropylphosphorodithioate.

14. A method for preparing a formulation of a biocidal thiophosphate composition substantially free of mercaptan from contaminants, said method comprising:
   (a) contacting a first solution comprising a member selected from the group consisting of alkali and alkaline earth metal iodates and hypochlorites in a first solvent with a second solution comprising said thiophosphate composition in a second solvent substantially immiscible with said first solvent, to oxidize substantially all mercaptan originally present in said biocidal thiophosphate composition;
   (b) recovering said second solution from said first solution; and
   (c) combining said second solution with an inert diluent or carrier.

15. A method in accordance with claim 14 in which said first solution comprises a member selected from the group consisting of alkali metal iodates and hypochlorites in a first solvent.

16. A method in accordance with claim 14 in which said first solution comprises a member selected from the group consisting of sodium and potassium iodates and hypochlorites in a first solvent.

17. A method in accordance with claim 14 in which said first solution comprises a member selected from the group consisting of sodium hypochlorite and potassium iodate in a first solvent.

18. A method in accordance with claim 14 in which said first solvent is water.

19. A method in accordance with claim 14 in which said first solution is aqueous sodium hypochlorite.

20. A method in accordance with claim 14 in which said first solution is aqueous sodium hypochlorite at a concentration ranging from about 0.1% to about 2.0% by weight.

21. A method in accordance with claim 14 in which said first solution is aqueous potassium iodate.

22. A method in accordance with claim 14 in which said first solution is aqueous potassium iodate at a concentration ranging from about 1.0% to about 5.0% by weight.

23. A method in accordance with claim 14 in which said second solvent is a member selected from the group consisting of paraffins, xylenes and aromatic naphtha.

24. A method in accordance with claim 14 further comprising combining said second solution with a polyol stabilizing agent.

25. A method in accordance with claim 14 further comprising combining said second solution with a polyol stabilizing agent selected from the group consisting of ethylene glycol, triethylene glycol, propylene glycol, dipropylene glycol, dibutylene glycol, hexylene glycol, and triethanolamine.

26. A method in accordance with claim 14 in which step (c) comprises impregnating porous granules with said second solution.

27. A method in accordance with claim 14 in which said thiophosphate composition comprises a thiophosphate compound having the formula

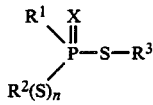

in which $R^1$ is methyl or ethyl, $R^2$ is tertiary alkyl having 4 to 6 carbon atoms, $R^3$ is tertiary alkyl having 4 to 6 carbon atoms, X is sulfur or oxygen, and n is zero or one.

28. A method in accordance with claim 14 in which said thiophosphate is S,S-(di-t-butyl) methylphosphorotrithioate.

29. A method in accordance with claim 14 in which said thiophosphate is S,S-(di-t-butyl) ethylphosphorodithioate.

30. A method in accordance with claim 14 in which said thiophosphate is N-(mercaptomethyl)phthalimide S-(O,O-dimethylphosphorodithioate).

31. A method in accordance with claim 14 in which said thiophosphate is O-ethyl S,S-dipropylphosphorodithioate.

32. A method for preparing a biocidal thiophosphate composition in a manner which inhibits mercaptan odor development from contaminants associated with said composition without affecting said thiophosphate having the formula:

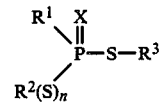

in which $R^1$ is ethoxy, methyl or ethyl, $R^2$ is primary or tertiary alkyl having 3 to 6 carbon atoms, $R^3$ is primary or tertiary alkyl having 3 to 6 carbon atoms, X is sulfur or oxygen, and n is zero or one, said method comprising:
(a) forming a solution by dissolving said thiophosphate and contaminants in a non-polar solvent selected from the group consisting of paraffins, xylenes and aromatic naphtha in the presence of a stoichiometric excess of iodine to convert substantially all of said contaminants to mercaptan, and
(b) removing said mercaptan from said composition or converting said mercaptan to a disulfide by the addition of a polar solvent selected from the group consisting of water, ethylene glycol, triethylene glycol, propylene glycol, dipropylene glycol, dibutylene glycol, hexylene glycol and triethanolamine, wherein removing said mercaptan comprises volatilizing said mercaptan and removing vapors so produced from said thiophosphate composition.

33. A method in accordance with claim 32 in which said thiophosphate is S,S-(di-t-butyl) methylphosphorotrithioate.

34. A method in accordance with claim 32 in which said thiophosphate is S,S-(di-t-butyl) ethylphosphorothrithioate.

35. A method in accordance with claim 32 in which said thiophosphate is O-ethyl S,S-dipropylphosphorodithioate.

* * * * *

UNITED STATES PATENT AND TRADEMARK OFFICE
CERTIFICATE OF CORRECTION

PATENT NO. : 4,948,787
DATED : August 14, 1990
INVENTOR(S) : Chia-Chung Chen, Richard H. Rider and Ray J. Lo It is certified that error appears in the above-indentified patent and that said Letters Patent is hereby corrected as shown below:

In Column 10, lines 23-24, delete the words "thiophosphate and contaminants and insert --composition--.

Signed and Sealed this

Twelfth Day of April, 1994

Attest:

BRUCE LEHMAN

Attesting Officer

Commissioner of Patents and Trademarks